United States Patent [19]
Tumey

[11] Patent Number: 5,674,262
[45] Date of Patent: Oct. 7, 1997

[54] PNEUMATIC COMPRESSION AND FUNCTIONAL ELECTRIC STIMULATION DEVICE AND METHOD USING THE SAME

[75] Inventor: David M. Tumey, Troy, Ohio

[73] Assignee: Kinetic Concepts, Inc., San Antonio, Tex.

[21] Appl. No.: 592,024

[22] Filed: Jan. 26, 1996

[51] Int. Cl.⁶ .............................. A61N 1/32; A61H 7/00
[52] U.S. Cl. .......................... 607/48; 601/151; 601/152; 128/DIG. 20; 607/49
[58] Field of Search ............. 607/48, 49; 128/DIG. 20; 601/151, 152

[56] References Cited

U.S. PATENT DOCUMENTS

| | | | |
|---|---|---|---|
| Re. 32,940 | 6/1989 | Gardner et al. | 128/DIG. 20 |
| 3,370,584 | 2/1968 | Girten . | |
| 4,499,900 | 2/1985 | Petrofsky | 607/48 |
| 4,586,510 | 5/1986 | Glaser | 607/48 |
| 4,597,384 | 7/1986 | Whitney | 601/152 |
| 4,622,973 | 11/1986 | Agarwala | 607/48 |
| 4,642,769 | 2/1987 | Petrofsky | 607/48 |
| 4,727,878 | 3/1988 | Levine | 607/50 |
| 4,735,205 | 4/1988 | Chachques | 607/2 |
| 4,750,499 | 6/1988 | Hoffer | 607/116 |
| 4,838,272 | 6/1989 | Lieber | 607/48 |
| 5,016,635 | 5/1991 | Graupe | 607/49 |
| 5,083,551 | 1/1992 | Addison, Jr. | 601/61 |
| 5,117,812 | 6/1992 | McWhorter | 128/DIG. 20 |
| 5,358,513 | 10/1994 | Powell, III | 607/48 |
| 5,396,896 | 3/1995 | Tumey et al. | 601/152 |
| 5,407,418 | 4/1995 | Szpur | 601/152 |
| 5,437,610 | 8/1995 | Cariapa et al. | 601/152 |
| 5,514,079 | 5/1996 | Dillon | 128/DIG. 20 |
| 5,575,762 | 11/1996 | Peeler et al. | 601/152 |
| 5,588,955 | 12/1996 | Johnson, Jr. et al. | 128/DIG. 20 |

OTHER PUBLICATIONS

Nicolaides et al, "Intermittent Sequential Pneumatic Compression of the Legs and Thromboembolism–Deterrent Stockings in the Prevention of Postoperative Deep Venous Thrombosis," *British Journal of Surgery*, Jul. 1983, pp. 21–25, vol. 94.

Primary Examiner—William E. Kamm
Assistant Examiner—Carl H. Layno
Attorney, Agent, or Firm—R. William Graham

[57] ABSTRACT

A device and method for stimulating blood flow velocity in a leg of the body for the prevention of Deep Vein Thrombosis in an effective and relatively painless manner which, in one case, includes an apparatus for compressing a foot in a manner to drive a substantial amount of blood from veins of the foot therein into blood vessels of the leg and an apparatus operably associated with the compressing apparatus for electrically stimulating leg muscles as the driven blood from the foot passes therethrough such that the muscles drivingly enhance blood flow velocity.

14 Claims, 3 Drawing Sheets

PNEUMATIC COMPRESSION AND FUNCTIONAL ELECTRIC STIMULATION DEVICE AND METHOD USING THE SAME

BACKGROUND OF THE INVENTION

This invention relates to a device for treating circulatory conditions within the body. More particularly, the present invention provides a device designed to prevent the formation of Deep Venous Thrombosis (DVT) in the lower extremities of non-ambulatory patients by causing blood in the feet, calves and optionally the thigh to be forcibly driven therefrom generating increased peak blood flow velocities in the deep vessels and the subsequent production of Endothelial Derived Relaxing Factor (EDRF).

EDRF (Nitric Oxide) is understood to be a naturally occurring vasodilator which is produced by yield shear stress on the endothelial lining of veins. These shear stresses are readily produced by increasing peak blood flow velocities through a cross section of the vessels. EDRF helps produce hyperaemia by dilating vessels and opening capillaries.

Previously, pneumatic compression devices have been utilized on a part of the human body for the purpose of increasing and/or stimulating blood flow. Such apparatuses have been made to adapt to an arm, hand, foot, calf and thigh. The apparatuses typically include an inflatable bladder or bladders connected to a pneumatic pump capable of delivering pressure within the bladder(s) to cause stimulation. Some apparatuses inflate and deflate in a cyclical fashion. The cycle rates and pressure have either been manually set by a clinician prior to application and use of the device or are controlled by a computer.

Conventional sequential pumping techniques use pneumatic compression which may be somewhat effective in evacuating blood from the deep and superficial system but fail to produce high blood flow velocities necessary for EDRF production. It is believed this is due to the fact that pneumatic compression is relatively slow in filling a large pneumatic bladder about an extremity with pressurized air.

Other devices also exist which stimulate blood flow. For example, artificial means such as Functional Electric Stimulation (FES) assists venous return.

Although attempts have been made at providing a satisfactory device for adequately stimulating blood flow velocities necessary for the production of EDRF, none of the existing devices have so provided. There remains a need for a device in the field of treating circulatory disease, namely, Deep Vein Thrombosis, which will effectively increase peak blood flow velocity in the blood vessels to stimulate the release of EDRF.

SUMMARY OF THE INVENTION

It is an object of the present invention to improve stimulation of blood flow velocity through blood vessels for the prevention of Deep Vein Thrombosis.

It is another object to improve the method and device in which blood flow is stimulated within lower extremities of the body.

Accordingly, the present invention is directed to a device for stimulating blood flow velocity in a leg of the body, which includes means for compressing a foot in a manner to drive a substantial amount of blood from veins therein into blood vessels of the leg and means operably associated with the compressing means for electrically stimulating leg muscles as the driven blood from the foot passes therethrough such that the muscles drivingly enhance blood flow velocity. The device further includes means operably connected to the compression means for sensing the blood fill status within the foot and triggering the compression means in response thereto. Also, included are means operably connected to the electrical stimulating means for sensing the blood fill status within the leg and triggering the electrical stimulating means in response thereto.

Another aspect of the invention is directed to a method of preventing DVT, which includes the steps of (a) compressing about the dorsal and sole of the foot at a first predetermined point when veins of the foot are filled with blood to provide a compressive force great enough to drive a substantial mount of blood from the venous plexus to superficial veins and deep veins of the leg and (b) electrically stimulating leg muscles surrounding the superficial and deep veins in the leg when the blood from the foot passed therethrough. The step (a) is further characterized such that the compressing about the foot is maintained for a predetermined period. The step (b) is further characterized such that the electrical stimulation initiated causes contractions in the calf muscles of the patient's leg to produce pulsatile driving of blood from the superficial and deep veins of the calf of the patient for a sufficient period to substantially drive the received blood therefrom. The method further includes the steps of (c) decompressing the foot to permit blood to substantially refill the veins of the foot and (d) ceasing electrical stimulation of the leg muscles. Finally, the invention includes the step (e) which includes repeating steps (a) through (d).

BRIEF DESCRIPTION OF THE DRAWINGS

FIG. 2a is a blown up portion of a part of the diagram of FIG. 2 depicting a series of high frequency impulses.

DETAILED DESCRIPTION OF THE PREFERRED EMBODIMENTS

Figure 1:
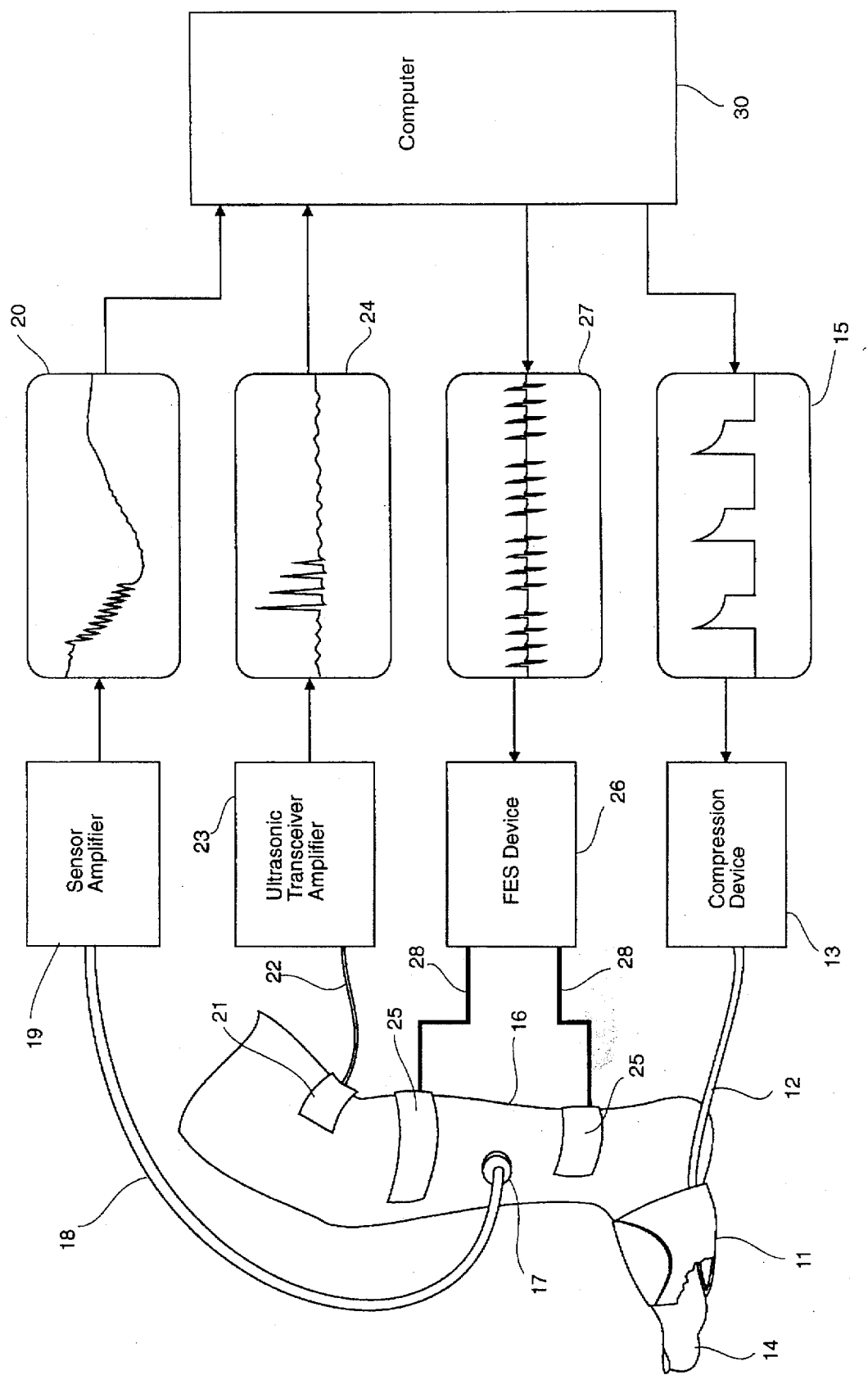
FIG. 1 is a schematic and block diagram of the device of the present invention.

The FES in combination with the pneumatic compression apparatus form integral parts of the present invention which are collectively extremely effective in driving blood through blood vessels in a leg to aid in the prevention of Deep Vein Thrombosis. From the disclosure presented herewith, it will be clear that FES of the leg muscles in combination with pneumatic compression about the foot can produce dramatic blood flow velocities not heretofore achieved.

The invention disclosed herein generates an increased blood flow velocity in an entirely new and unique way. More particularly, the deep and superficial vessels of the foot, calf(and optionally the thigh) are emptied rapidly through a sequential combination of pneumatic compression about the foot and electrical stimulation of the leg muscles. Blood within the veins of the foot is driven out by the application of pneumatic pressure in a bladder substantially covering the foot. Blood in the veins of the leg is driven out though a squeezing of the gastrocnemius muscle group by direct posterior electrical stimulation thereof The present invention generates a series of rapid pulsatile contractions in succession each of which cause blood to spurt up the deep vein system and out of the calf, while at the same time, the superficial system is emptied into the deep vein system. These phenomena are confirmed by both blood Doppler readings taken at the popliteal vein, and photo-plethysmographic analysis of the microvascular bed of the calf. Thus, the use of the FES technique in combination with pneumatic foot compression disclosed herein provides a far safer, less costly and optimally effective DVT prophylaxis.

The preferred embodiment of the present invention includes the utilization of sensors in a closed loop paradigm for optimization of the stimulation waveforms for each individual patient. Every patient has an individual and variable physiology with respect to the emptying and filling characteristics of their foot, calf and thigh. Since each person's physiology is essentially different from the next, it is very useful to incorporate a biofeedback system with the current invention and some intelligent algorithms to create a smart-system that has the ability to adapt and compensate for the individual variations which will be encountered between patients. This self-optimizing closed loop paradigm has been implemented by the inventor previously with respect to a footpump device disclosed in U.S. Pat. No. 5,386,896, the subject matter of which is incorporated herein by reference.

The pneumatic foot pump employed enables blood to be substantially driven from the veins of the foot, thus priming the vessels of the leg, particularly the calf Rapid pneumatic compression of the veins of the foot produces an increased peak blood flow velocity in the deep veins and stimulates the production of EDRF. It is found in the present invention that blood flow velocity can be more effectively maintained and enhanced with the use of FES of the leg muscles and computer incorporating intelligent algorithms of the type described in U.S. Pat. No. 5,386,896 incorporated herein by reference to provide biofeedback within the leg, particularly the foot and calf.

The dynamic timing between the foot compression and calf muscle stimulation will be continuously sensed and generated by the computer such that the blood flow velocity is maximized. In addition, while one foot compression period may last for about 30–50 seconds, the electrical stimulation of the calf muscles utilizes a series of relatively quick stimulating pulses causing a number of muscle contractions to create a number of peaks of high velocity blood flow which again cause increased stimulation of EDRF.

Referring now to the drawings, FIG. 1 depicts the system diagram for the preferred arrangement of the present invention. A fluid bladder 11 is operatively connected to a small diameter plastic hose 12 and a cyclical fluid compression device 13. The compression device 13 provides impulses of compressed air, for example, that cause bladder 11 to inflate and apply compressive forces to the foot 14 of the patient causing blood to be rapidly driven from the superficial veins on the top and sides of the foot 14 and the deep veins, in the plantar arch region of the foot 14, such veins also are referred to as the venous plexus. These plantar veins are primarily fed through venae-comites of the lateral plantar artery and are plexiform in arrangement. The blood that is ejected from the foot 14 upon application of the rapid compressing force is expelled up the deep veins (mainly the posterior and anterior tibial veins) in addition to the long and short saphenous veins. This increased peak blood flow velocity in the deep system causes the production of EDRF and at the same time, the total blood volume of the calf 16 increases slightly as the blood leaving the foot 14 enters the calf 16.

The compression device 13 is operatively connected to a computer 30 for controlling the onset and cessation of pressure application based on an integral control algorithm within a computer, such as a neural network-based computer, as described in U.S. Pat. No. 5,396,896 incorporated herein by reference. The impulses of compressed fluid are applied in a generally cyclical manner such as is depicted in 15 with a predetermined period provided by the computer 30 as described above.

When the venous plexus is substantially filled with blood and the compression is applied to the patient's foot 14, a substantial mount of blood (approx. 10–20 cc) is driven through the deep and superficial veins into the patient's calf region 16 causing changes in the calfs blood volume. In addition, the column of blood moving in the deep system (even though it moves only a few centimeters) generates a high peak blood flow velocity in the deep proximal veins such as the popliteal and common femoral vein.

A photo-plethysmographic sensor 17 is employed to monitor the mount of change in blood volume of the calf. The sensor 17 is nominally adhering to the surface of the skin approximately 10 cm proximal from the ankle using a doughnut shaped adhesive ring which utilizes three infrared light emitting diodes (LED's) and one infrared phototransistor to measure the amount of blood in the microvascular bed approximately one to two mm beneath the surface of the skin. This measurement is believed to be indicative of the volume of blood in the region over which the sensor is placed, and in this case is indicative of the volume of blood in the patient's calf 16. The sensor 17 is operatively connected to an electrical cable 18 and an electronic amplifier 19 which amplifies the weak electrical signal from the photo-plethysmographic sensor 17. An example output waveform signal obtained from the sensor 17 is shown in 20 and is typical of what is normally observed for a patient using the full system of foot and calf compression as shown in FIG. 1.

For example, the calf pump could be engaged when the amount of blood volume in the calf has reached some maximum point relative to its normal resting baseline. In addition, for simpler implementation, an average delay time (taken from a statistically meaningful population of patients) between the inflation of the foot bladder and optimal FES calf pump stimulation could be utilized to provide adequate results.

The output signal as depicted in 20 is provided to the computer 30 as an input through an operative connection between the sensor amplifier 19 and the computer 30. As described above, the sensor information is utilized by the computer's algorithms in controlling the amount and timing of the application of pressure and electrical stimulation to the patient.

In addition to the plethysmographic sensor 17, an additional sensor 21 designed to measure blood flow velocity such as a Doppler ultrasonic sensor can be employed. This sensor 21 is depicted in FIG. 1 as being placed beneath the knee enabling it to measure the velocity of blood in the popliteal vein. Sensor 21 is operatively connected to an electrical cable 22 and an ultrasonic transceiver and amplifier 23. The sensor 21 is used to ascertain the peak blood flow velocity in a vein and provide a signal indicative of the same.

An example output waveform signal obtained from the sensor 21 is shown in 24 and is typical of what is normally observed for a patient using the system of compressing the foot 14 and electrically stimulating the calf 16 as shown in FIG. 1. As before, the output signal as depicted in 24 is provided to the computer 30 as an input through an operative connection between the sensor amplifier 23 and the computer 30. As before, the sensor information can be utilized by the computer's algorithms in controlling the amount and timing of the application of pressure and electrical stimulation to the patient.

In order to provide the necessary contraction of the patient's calf muscle, an FES device 26 is employed that is operatively connected to the patient's calf 16 through a communicating electrical cable 28 and a plurality of conducting electrodes 25 which are placed on the surface of the patient's skin. The electrodes 25 can be fabricated from a conducting foil and a conducting hydrogel adhesive, or from any other suitable conducting medium or could be one of the myriads of conventional electrodes currently being utilized for TENS devices such as those produced by the 3M company. The general size and shape of the electrodes 25 should be selected to ensure proper stimulation of the calf muscles, a suitable configuration being an electrode that measures approximately one to three inches wide by four to seven inches long. The electrodes 25 are connected to the communicating electrical cable 28 and are disposable after a single patient use. The FES device 26 is configured with a small battery powered device that operates in a similar fashion to a transcutaneous electro-neural stimulator unit (TENS) commonly employed for the management and reduction of pain. The electrodes can be positioned in such a way as to cause maximal contraction efficiency of the gastrocnemius muscle group. The stimulation waveform utilized in the present invention has been chosen to provide the largest amount of muscular contraction in the calf with the minimum amount of discomfort. For this reason, the stimulation parameters closely resemble that of an actual neural impulse signal normally sent by the motor cortex of the brain and relayed through the motor nerves. By carefully digitizing, tailoring and synthesizing the neural impulses generated by the stimulation unit, a strong contraction can be produced in most subjects without causing any appreciable amount of pain.

The stimulation waveform provided to the patient's calf 16 is depicted in 27. It can be seen that an individual contraction is created by the transmission of a series of neural impulses provided in rapid succession. The frequency chosen for the individual stimulating impulses should be high enough to produce a single continuous muscle contraction. It is thought that this arrangement of using a packet of pulses to produce the stimulation rather than a steady direct current potential square wave or sine wave contributes greatly to the painlessness of the FES device 26 disclosed in the present invention. The FES device 26 is operatively connected to the computer 30 and a stimulation onset is regulated by in a predetermined manner according to the patient's need or to maximize blood flow velocity. The stimulation can consist of one or more rapid contractions (each contraction consisting of a series of neural impulses) to produce the desired ejection of blood from the calf. As described above, the information obtained from the sensing means 17 and 21 can be utilized to control the frequency and number of stimulated compressions provided to the patient's calf 16.

Each compressive contraction is produced by sending a series of fast rise-time pulses from the FES device 23 at between 15 and 100 cycles per second. The frequency of stimulation is fast enough that the result is a single contraction in the patient's calf muscle. Thus, a packet or group of synthesized pulses from the FES device constitutes one single compressive contraction. The contraction force is applied for less than one second and then the stimulation is abated for between one and three seconds and the next contraction is initiated. Each contraction is very rapid and produces high velocity blood flow within the vessel of the patient's calf. The present invention utilizes an extremely fast rise time (approx. 100 msec) and a short 400–700 msec contraction duration. In addition to deep venous emptying, blood in the superficial system is squeezed into the deep system through the perforating veins. Any number of contractions can be provided in the series, for example from between one and ten contractions, or, the invention could also make use of the plethysmographic sensing means attached to the patient's calf as described above to measure the volume of blood in the calf and cease pumping once a sufficient amount of blood had been ejected from the cat. Therefore, the invention could implement the calf pumping with a single contractile force, or a plurality of timed contractions which are either automatically controlled or set at some predetermined interval.

Figure 2:
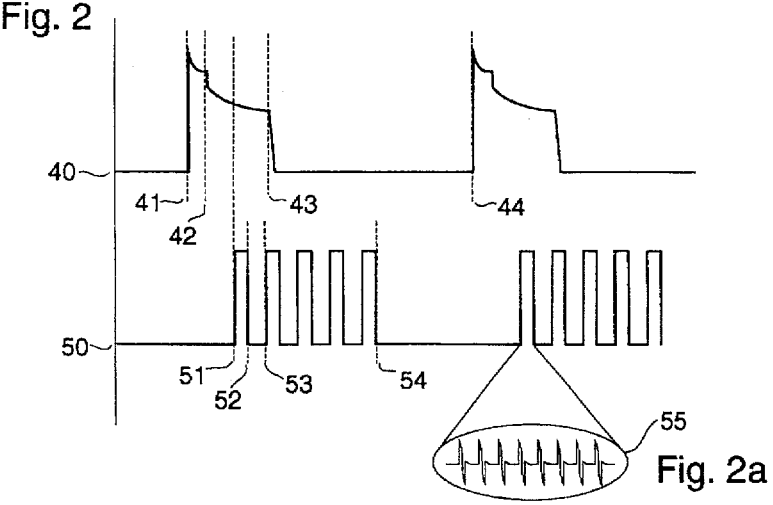
FIG. 2 is timing diagram illustrating the timing sequence of the present invention.

FIG. 2 depicts the system timing diagrams for the embodiment as described in FIG. 1. It is to be noted that the scope of the invention should not be limited to the timed order of events presented in FIG. 2, as this depiction is only one of many possible configurations suitable for the present invention. The FES waveform 55 is shown in the exploded view of FIG. 2a. From FIG. 2a it can be seen that each contraction impulse comprises a series of high frequency neural impulses. Compression is applied to the patient's foot 14 via a compressed fluid bladder 11 as described above and compression is stimulated in the patient's calf 16 via muscle contractions caused by direct electrical stimulation of the muscles also as described above. In FIG. 2, the pressure impulse waveform applied to the patient's foot 14 is depicted in 40, while the stimulation waveform applied to the patient's calf is depicted in 50.

At a first predetermined time 41, a fluid valve is opened in the cyclical fluid compression device 13, which causes a compressed fluid such as air to inflate the bladder 11 and thus compress the patient's foot 14. At a second predetermined time 42, the inflation valve is closed and the pressure is maintained in the bladder with the exception of some inevitable leaking either through the compression device 13 or purposeful ventilation holes in the bladder 11. The period between 41 and 42 can be regulated to control the amount of compressive force applied to the patient's foot.

An increase in the length of this period results in an increase in fluid pressure in the bladder 11. It has been demonstrated that a substantial amount of blood in the patient's foot 14 is driven from the foot's veins within the first 100–400 msec after pressure is applied, and the effect of holding the pressure generates an increase in arterial flow due to some well-established phenomena. Holding the pressure on the foot 14 will also minimize venous reflux that could occur when the calf stimulation is applied.

At a third predetermined point 51, which will preferably occur after the first predetermined point 41, the first of a series of stimulation impulses are applied to the patient's calf 16 causing muscle contraction. The number of contractions can be varied from, for example one to ten, the only requirement being that the contractions be halted in time to allow the calf 16 and foot 14 to properly refill with blood. At a stimulation interval or period defined by the time between 51 and 52, the stimulation is removed for a period of time defined by the interval between 52 and 53, when the next stimulation impulse begins. The strength of contraction can be controlled by varying the amplitude of the neural stimulation impulses 55, and the interval between 51 and 52. The period between 52 and 53 can be chosen for optimum efficiency and will normally be in the range of one to three seconds.

At a fourth predetermined point 43, which will preferably occur after a substantial amount of the blood has been driven from the veins of the calf 16 to minimize the risk of venous reflux, the fluid pressure being maintained in the bladder 11 around the patient's foot 14 is vented to the atmosphere. The period between 42 and 43 is normally between two and four seconds and should be held long enough to allow the majority of blood in the deep venous system of the calf 16 to be driven therefrom.

At a fifth predetermined point 54, which usually occurs after the point 43 but may occur simultaneously with or after the point 43, the stimulation is halted. The time period between either 43 or 54, whichever comes later, and 44 is provided to allow the patient's calf 16 and foot 14 to refill from arterial blood flow. During this time, no compression or stimulation is provided.

At a sixth predetermined point 44 which is normally between 20 and 60 seconds from point 41, the entire cycle as described above repeats for the duration the system is utilized by the patient. All of the predetermined points depicted in FIG. 2 are preferably generated by the computer 30 through its intelligent controlling algorithms and sensing means 17 and 21.

Figure 3:
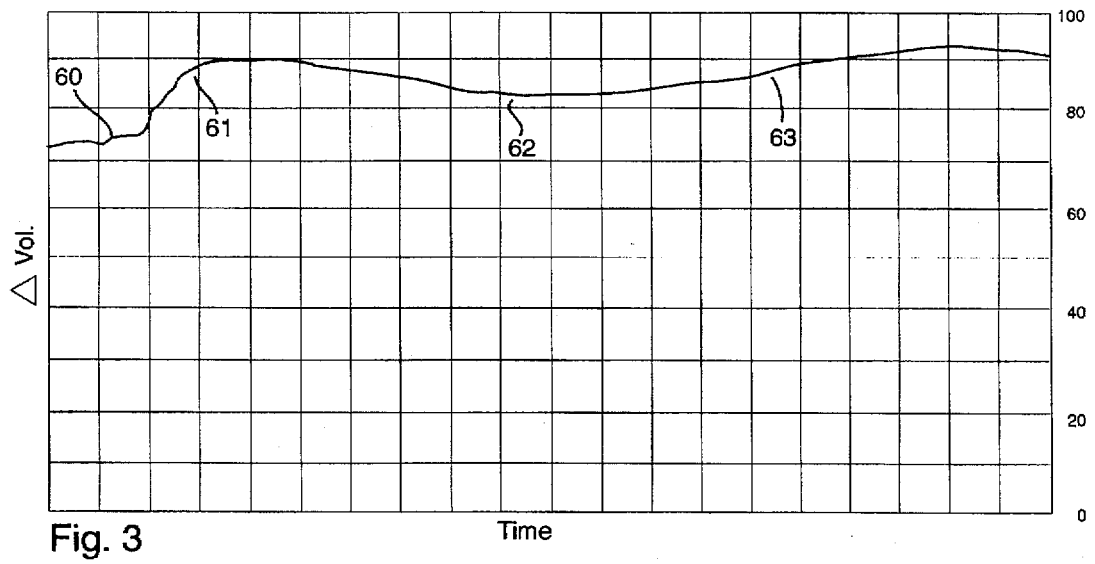
FIG. 3 is a plot diagram of blood volume in a leg with respect to pressure applied to the foot.

FIG. 3 depicts the sensor data obtained from the photoplethysmographic sensor 17 located on the patient's calf 16 and represents a plot of the blood volume in the leg with respect to pressure applied to the foot. This recording was made showing the response of the sensor 17 to the application of pressure to the patient's foot 14 alone, thus providing a baseline to which the combined application of foot pressure and calf stimulation can be compared. As can be seen at interval point 60, the compressed fluid pressure is applied to the patient's foot 14. Blood moving from the foot 14 toward the heart through the calf 16 causes a slight rise in the calf's total blood volume as is evidenced by the curve traced by 60, 61 and 62. The peak increase in blood volume can be seen at point 61 which indicates blood volume in the calf 16 and it diminishes between points 61 and 62. After the pressure is relieved from the foot 14, the foot 14 refills and is ready for another compression impulse between the points 62 and 63. At 63 the sensor data has returned to its baseline levels. This cycle repeats each time the foot 14 is compressed in the above described manner. The chart speed of this and all subsequent recordings was three seconds per division.

Figure 4:
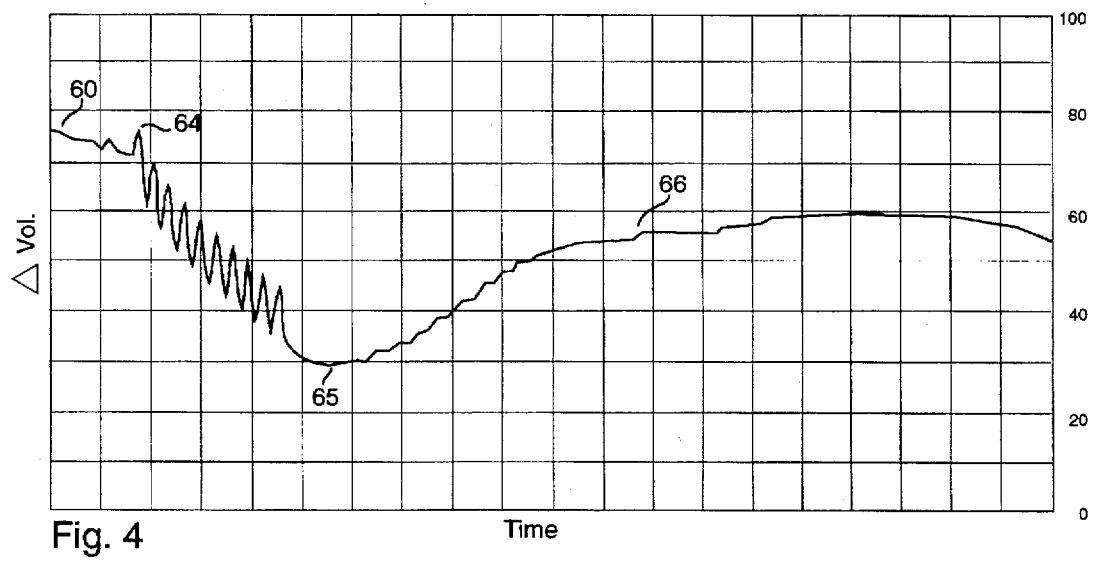
FIG. 4 is a plot diagram of blood volume in a leg with respect to pressure applied to the foot in conjunction with electrical stimulation of muscles in the leg.

FIG. 4 depicts the same sensor data obtained from sensor 17 located on the patient's calf 16 and represents a plot of the blood volume with respect pressure applied to the foot 14 in conjunction with electrical stimulation of the calf 16. This recording was made showing the response of the sensor to the application of pressure to the patient's foot 14 in combination with electrical stimulation of the calf 16. As can be seen in FIG. 3, point 60 of FIG. 4 corresponds to 41 in FIG. 2 and represents the onset of the fluid pressure in the bladder 11. The FES is applied to the calf 16 at a point which corresponds to 51 in FIG. 2. Note the step curve traced between points 64 and 65 in FIG. 4. This is caused by the pulsatile blood ejection that results from the stimulation technique employed. At point 65, the calf stimulation is abated and the calf 16 is allowed to refill during the period 65 and 66. At point 66, the calf 16 and foot 14 have refilled, the sensor 17 has returned to its baseline levels and the system is ready for another cycle. It is to be noted that the increase in peak blood volume driven from the calf 16 for the combined stimulation relative to the increase in volume for the foot 14 compression alone is nearly 255% which is an extremely good indication that the superficial venous system of the calf is being efficiently evacuated.

Figure 5:
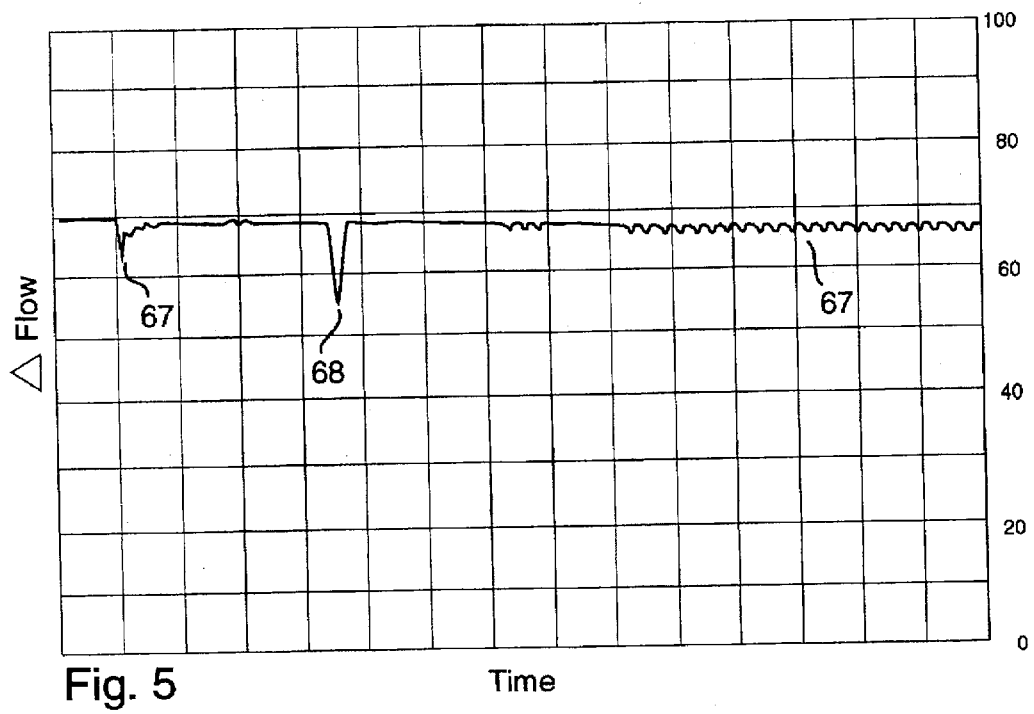
FIG. 5 is a plot diagram of blood flow velocity in a leg with respect to pressure applied to the FIG. 6 is a plot diagram of blood flow velocity in a leg with respect to pressure applied to the foot in conjunction with electrical stimulation of muscles in the leg.

FIG. 5 depicts sensor data obtained from the blood flow Doppler sensor 21 at the popliteal vein of the patient's leg for foot compression alone (baseline). The normal venous return can be seen in 67 which is pulsatile due to the action of the heart and the arterial blood flow. The peak levels of this signal are indicative of the velocity at which the blood is moving in the vessel, higher peak indicating higher velocities. At a point corresponding to point 41 of FIG. 2 when the compressed fluid is applied to bladder 11 around the patient's foot, within 100–400 msec, a large peak in blood velocity is recorded 68. This single large peak represents the blood driven from the foot 14 into the deep system of the calf 16 (as measured at the popliteal vein at the knee). As described above in detail, this large peak in blood flow velocity causes the endothelium lining the vessel walls to produce EDRF which is a vasodilator. This powerful substance will act to improve circulation in the patient by causing vessel diameters to increase and also open collateral circulation. After peak 68, the sensor data quickly returns to a baseline and indicates again the normal flow rate velocities 67 caused by arterial blood flow.

Figure 6:
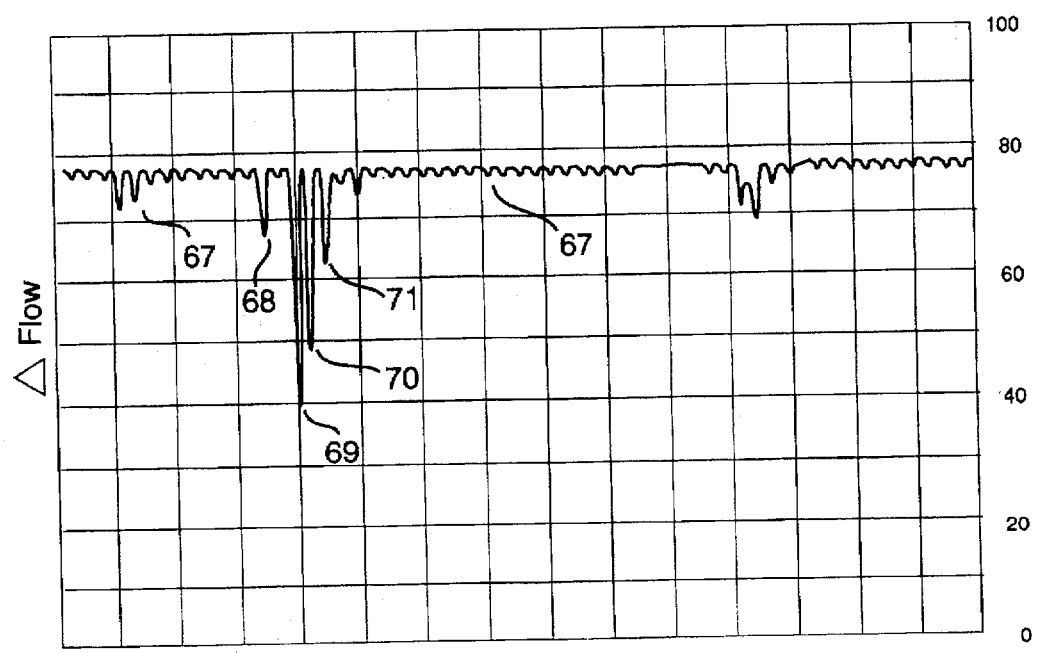

FIG. 6 depicts sensor data obtained from the blood flow Doppler sensor 21 at the popliteal vein of the patient's leg for foot and calf stimulation. The normal venous return can be seen in 67 which is pulsatile due to the action of the heart and the arterial blood flow. The peak levels of this signal are indicative of the velocity at which the blood is moving in the vessel, exactly as described above. At point 41, as described above, pressure is applied to the patient's foot 14 generating the peak 68 exactly as in FIG. 5. At a point corresponding to 51 in FIG. 2, as described above, the electrical stimulation is initiated for the calf 16, causing the additional peaks 69, 70 and 71. As before, these huge increases in peak blood velocity trigger the production of EDRF. It is important to note that the peaks produced by the FES decrease in amplitude as less blood is available in the calf for pumping during subsequent contractions. The first peak contributed by the FES 69 is seen to be the largest and can often produce blood flow velocities 250% higher than those produced by the foot compression. After peak 71, the sensor data quickly returns to the baseline and indicates again the normal flow rate velocities 67 caused by arterial blood flow. In addition, there is a plurality of peaks produced by the combined system wherein the blood flow through the calf by electrical stimulation of calf muscles capitalizes upon the initial blood flow generated from the foot compression. Both of these factors will contribute to an increased production of EDRF which is considered to be very beneficial to the patient and is not heretofore accomplished. It is important to note that pneumatic calf compression devices are unable to produce these high blood velocity peaks.

In conclusion, the present invention provides a novel combination which is shown to have marked improvement in the field of circulatory stimulation. Thus, the present invention utilizes a unique type of painless compression and stimulation that allows the system to be utilized with an awake and fully cognizant patient.

The above described invention is set forth for exemplary purposes only and is not intended to be limiting in scope of the claims appended hereto. Accordingly, modifications, derivations and improvements will be readily apparent to those skilled in the art and should be encompassed by the claims hereto.

What is claimed is:

1. A device for stimulating blood flow velocity in a leg of the body, which includes:

means for compressing a foot in a manner to drive a substantial mount of blood from veins of the foot therein into blood vessels of the leg; and means operably associated with the compressing means for electrically stimulating leg muscles as the driven blood from the foot passes therethrough such that the muscles drivingly enhance blood flow velocity.

2. The device of claim 1, which further includes means operably connected to the compression means for sensing the blood fill status within the foot and triggering the compression means in response thereto.

3. The device of claim 1, which further includes means for operably connecting to the electrical stimulating means for sensing the blood fill status within the leg and triggering the electrical stimulating means in response thereto.

4. A method of preventing DVT, which includes the steps of:

(a) compressing about the dorsal and sole of the foot at a first predetermined point when veins of the foot are filled with blood to provide a compressive force great enough to drive a substantial amount of blood from the veins to deep veins and superficial veins of the leg; and (b) electrically stimulating leg muscles surrounding the superficial and deep veins in the leg when the blood from the foot passed therethrough.

5. The method of claim 4, wherein the step (a) is further characterized such that the compressing about the foot is maintained for a predetermined period.

6. The method of claim 5, wherein the step (b) is further characterized such that the electrical stimulation is initiated causing contractions in the calf muscles of the patient's leg to produce pulsatile driving of blood from the superficial and deep veins of the calf of the patient for a period sufficient to substantially drive the received blood therefrom.

7. The method of claim 6, which further includes the steps of (c) decompressing the foot to permit blood to substantially refill the venous plexus and (d) ceasing electrical stimulation of the leg muscles.

8. The method of claim 7, which further includes a step (e) which includes repealing steps (a) through (d).

9. A method for preventing Deep Vein Thrombosis in a leg of a patient, which includes the steps of (a) positioning a charged electrical stimulating device adjacent the leg; and (b) electrically discharging said stimulating device in a manner to cause pulsatile contractions in a leg wherein each said contraction is characterized to include a relatively rapid impulse onset and relatively short duration.

10. The method of claim 9, wherein prior to the step (a) said method further includes the step of applying a compressive force about a foot of the patient to drive blood from the foot to the leg.

11. The method of claim 9, wherein said duration is less than 3 seconds.

12. A method for stimulating muscle contraction in a patient for the purpose of increasing blood flow and preventing Deep Vein Thrombosis, which includes the steps of:

(a) sensing motor neural impulses;

(b) synthesizing said sensed impulses to produce an electrical waveform corresponding thereto; and (c) employing said waveform into a computer based charged electrical stimulating device to cause a discharge of said electrical stimulating device which stimulates a contraction of a leg muscle of a patient emulating said motor neural impulses and wherein said contractions are further characterized to include a relatively rapid onset and relatively short duration.

13. The method of claim 12, wherein said duration is less than 3 seconds.

14. The method of claim 12, wherein prior to the step (a) said method further includes the step of applying a compressive force about a foot of the patient to drive drive blood from the foot to the leg.

* * * * *